United States Patent
Dunlop (10) Patent No.: US 9,386,926 B2
(45) Date of Patent: Jul. 12, 2016

(54) BLOOD PRESSURE MONITOR

(71) Applicant: Colin Dunlop, East Ryde (AU)

(72) Inventor: Colin Dunlop, East Ryde (AU)

( * ) Notice: Subject to any disclaimer, the term of this patent is extended or adjusted under 35 U.S.C. 154(b) by 0 days.

(21) Appl. No.: 14/187,935

(22) Filed: Feb. 24, 2014

(65) Prior Publication Data

US 2014/0171813 A1    Jun. 19, 2014

Related U.S. Application Data (63) Continuation of application No. 12/303,086, filed as application No. PCT/AU2007/000741 on May 30, 2007, now abandoned.

(30) Foreign Application Priority Data

May 30, 2006    (AU) .................................. 2006902912

(51) Int. Cl.
| | |
|---|---|
| A61B 5/02 | (2006.01) |
| A61B 5/021 | (2006.01) |
| A61B 5/022 | (2006.01) |
| A61B 5/0235 | (2006.01) |
| A61B 5/00 | (2006.01) |
| A61B 5/20 | (2006.01) |

(52) U.S. Cl.
CPC ............. *A61B 5/02141* (2013.01); *A61B 5/022* (2013.01); *A61B 5/0235* (2013.01); *A61B 5/02225* (2013.01); *A61B 5/02233* (2013.01); *A61B 5/742* (2013.01); *A61B 5/746* (2013.01); *A61B 5/205* (2013.01)

(58) Field of Classification Search
USPC .................................................. 600/485–515
See application file for complete search history.

(56) References Cited

U.S. PATENT DOCUMENTS

| | | | |
|---|---|---|---|
| 2,452,799 A | | 11/1948 | Speaker et al. |
| 3,536,062 A | | 10/1970 | Horn |
| 3,654,915 A | * | 4/1972 | Sanctuary ...................... 600/495 |
| 3,730,172 A | * | 5/1973 | Buddecke et al. ............ 600/493 |
| 3,811,439 A | | 5/1974 | Brown |
| 3,903,872 A | | 9/1975 | Link |
| 4,009,709 A | | 3/1977 | Link et al. |
| 4,074,711 A | | 2/1978 | Link et al. |
| 4,106,498 A | | 8/1978 | Haney |
| 4,154,238 A | | 5/1979 | Link |
| 4,174,707 A | | 11/1979 | Link et al. |
| 4,178,918 A | * | 12/1979 | Cornwell ...................... 600/495 |
| 4,206,764 A | | 6/1980 | Williams |
| 4,263,918 A | | 4/1981 | Swearingen et al. |
| 4,427,013 A | | 1/1984 | Nunn et al. |
| 4,437,470 A | | 3/1984 | Prost |
| 4,469,107 A | | 9/1984 | Asmar et al. |
| 4,779,626 A | * | 10/1988 | Peel et al. ...................... 600/488 |
| 4,940,059 A | | 7/1990 | Voelz |
| 5,025,793 A | | 6/1991 | Richley et al. |
| 5,099,851 A | * | 3/1992 | Hata et al. ...................... 600/485 |
| 5,634,467 A | | 6/1997 | Nevo |
| 6,694,821 B2 | | 2/2004 | Yamakoshi et al. |

* cited by examiner

*Primary Examiner* — Michael Kahelin
*Assistant Examiner* — Mitchell E Alter
(74) *Attorney, Agent, or Firm* — Knobbe, Martens, Olson & Bear, LLP (57) ABSTRACT

The present invention relates to an apparatus and method for facilitating blood pressure measurement. An additional fluid reservoir is arranged to be connected in fluid communication with the blood pressure cuff. The fluid reservoir provides an additional, compliant volume to the fluid volume of the cuff, facilitating blood pressure measurement, particularly for small volume cuffs.

13 Claims, 6 Drawing Sheets

FIG. 1

Illustration of the error expected for indirect blood pressure when the cuff width deviates from 40% of the member circumference.

BLOOD PRESSURE MONITOR

FIELD OF THE INVENTION

The present invention relates to the measurement of pressure and, more particularly, but not exclusively, to a method, system and apparatus for measuring systemic arterial blood pressure.

BACKGROUND OF THE INVENTION

Blood pressure is an important measurement in both veterinary and human medicine. For example, a frequent determination of blood pressure is routine during anaesthesia. It is also routine to measure blood pressure to obtain an indication of the general health of a patient.

Non-invasive measurement of arterial blood pressure is almost always carried out utilising a distensible cuff or a distensible bladder enclosed in an unyielding cuff. The cuff is placed around a limb or extremity of a patient, and is then inflated until blood flow through an underlying blood vessel (usually an artery) is occluded.

The cuff is then deflated in a controlled manner and measurements taken to detect occurrence of blood flow through the vessel. The measurements are generally to determine three important parameters:
1) Systolic arterial pressure (identified as the onset of blood flow following occlusion);
2) Diastolic arterial pressure (oscillations in the cuff have ceased i.e. full blood flow through the blood vessel without any occlusion);
3) Mean arterial pressure (the "mean" between the diastolic and systolic pressure—may be calculated or measured).

In cuff blood pressure measurement, the size of the cuff relative to the limb is critical for accuracy of the measurement. For human adults, the width of the cuff is generally about 40% of the circumference of the limb. Slight variations is the size of the limb from patient to patient, for an adult human, do not have a great effect on the accuracy of the measurement (usually only a few percentage points). As the size of the limb or extremity becomes smaller, however, and as a smaller cuff must be used in these cases, accuracy of measurement is more difficult to achieve and variations between the size of patients for a particularly small cuff size have much more of a pronounced effect on measurement accuracy. For infants and small animals, for example, measurement errors can be so significant as to render any blood pressure reading so inaccurate as to be useless. Further, use of a smaller volume cuff will lead to more errors, regardless of variations between limb size. A smaller volume cuff allows less scope for a gradual release of pressure to enable the blood pressure reading to be determined accurately.

SUMMARY OF THE INVENTION

In accordance with a first aspect, the present invention provides an apparatus for facilitating blood pressure measurement, including a fluid reservoir arranged to be connected in fluid communication with a blood pressure cuff, the fluid reservoir being arranged to provide an additional fluid volume to the fluid volume of the cuff during measurement of blood pressure of a patient.

In an embodiment, the fluid reservoir is arranged to change in volume when a change of pressure is applied. When the fluid reservoir changes in volume it is arranged to add little or no pressure back into the system.

In an embodiment, the use of the fluid reservoir advantageously results in the blood pressure measurement being less prone to error than without use of the fluid reservoir. It is particularly advantageous when blood pressure of a small human or animal patient is being measured. In an embodiment, by utilising the fluid reservoir, the effective volume of a small cuff may be significantly increased, thereby resulting in a slower drop in pressure once the bleed valve is opened, allowing for more accurate point readings for systolic or diastolic pressure to be taken and repeatedly detected.

In an embodiment the fluid reservoir has a compliance, and in an embodiment the compliance is sufficient such that oscillations of pressure from the blood pressure cuff are not significantly damped by the fluid reservoir.

In an embodiment, the degree of compliance is such that the pressure on the fluid reservoir during any blood pressure measurement will not exceed the fluid reservoir's Critical Opening Pressure.

In an embodiment, the degree of compliance is such that the fluid reservoir will change volume when a change in pressure is applied, but does not add any significant pressure back into the system (i.e. the fluid reservoir exerts little or no elastic force through the desired operating range for measurement of blood pressure). The fluid reservoir allows for a change in volume, with little or no change in pressure in the system. If the change in volume resulted in additional pressure in the system, this would be likely to reduce the accuracy of the pressure reading.

In an embodiment, the appropriate compliance of the fluid reservoir must be effective over a working range for measurement of blood pressure. In an embodiment a working range of pressure is from 55 mm Hg to 185 mm Hg.

In an embodiment, the fluid reservoir is formed by a fluid container having at least one expandable wall in order to provide compliance. In an embodiment, the fluid container is of plastics material. In an embodiment the fluid reservoir is of silicone.

In one embodiment, the fluid reservoir is formed by a expandable container mounted within a rigid housing, so that the expandable container can not expand beyond the volume of the rigid housing.

In an embodiment, a further advantage of the provision of the fluid reservoir is improvement of accuracy by reducing motion artefacts in the detected pressure. With smaller cuffs, in particular, a sensitive pressure transducer is required for blood pressure measurement—motion artefacts may easily be mistaken for systole. By adding the additional fluid volume, motion artefacts are dampened plus the need for sensitive pressure measurement devices may be avoided.

In accordance with a second aspect, the present invention provides a system for measuring blood pressure, including an apparatus in accordance with the first aspect of the invention and a blood pressure cuff, the fluid reservoir being arranged to be connected in fluid communication with the blood pressure cuff.

In accordance with a third aspect, the present invention provides an automated system for measuring blood pressure, including a controller for controlling the provision of fluid under pressure to a blood pressure cuff, a display for providing a reading of blood pressure value, and an apparatus in accordance with the first aspect of the invention, the fluid reservoir being arranged to be connected in fluid communication with the blood pressure cuff.

In an embodiment, the automated system further includes a pump for providing fluid to a line also connecting in fluid communication with the blood pressure cuff and fluid reservoir.

In accordance with a fourth aspect, the present invention provides a method of measuring blood pressure using a blood pressure cuff, including the step of providing an additional fluid volume in fluid communication with the blood pressure cuff. In an embodiment, the additional fluid volume is arranged to change the effective volume of the blood pressure cuff when a change of pressure is applied.

In an embodiment, the additional fluid volume changes in the effective volume of the cuff, it is arranged to add little or no pressure back into the system.

In an embodiment, the additional fluid volume has a compliance. In an embodiment, the compliance is sufficient such that oscillations of pressure from the blood pressure cuff are not significantly damped.

In an embodiment, the additional fluid volume is formed by a fluid reservoir. In an embodiment, the compliance in such that the pressure on the fluid reservoir during any blood pressure measurement will not exceed the fluid reservoir's Critical Opening Pressure.

In an embodiment, the compliance is such that a fluid reservoir provides a variable volume with changes in pressure, but does not add any significant pressure. In an embodiment, there is little or no elastic force provided by the fluid reservoir.

Embodiments of the present invention may be utilised for other applications than systemic arterial blood pressure measurement. Embodiments of the invention are particularly useful for measuring pressure where small pressure changes are involved in small volume situations. This is because embodiments of the present invention operate to increase the relative volume of the system, and therefore increase accuracy of the pressure measurement.

In accordance with a fifth aspect, the present invention provides an apparatus for facilitating pressure measurement, including a fluid reservoir arranged to be connected in fluid communication with a pressure measuring device, the fluid reservoir being arranged to provide an additional fluid volume to a fluid volume of the pressure measurement device during measurement of pressure.

In an embodiment, the pressure measurement device is a device which includes a variable volume.

In an embodiment, the fluid reservoir has a compliance, and in an embodiment the compliance is such that any pressure on the fluid reservoir during pressure measurement will not exceed the fluid reservoir's Critical Opening Pressure.

In an embodiment, the degree of compliance is such that the fluid reservoir will change volume when a change in pressure is applied, but does not add any significant pressure back into the system (i.e. the fluid reservoir exerts little or no elastic force through the desired operating range for measurement of pressure).

In an embodiment, the fluid reservoir is formed by a fluid container having at least one expandable wall in order to provide compliance.

In an embodiment, the pressure measurement application is pressure in relation to an animal or human body.

In accordance with a sixth aspect, the present invention provides a method of measuring pressure, including the step of providing additional fluid volume in fluid communication with a pressure measurement device having a fluid volume.

BRIEF DESCRIPTION OF THE DRAWINGS

Features and advantages of the present invention will become apparent from the following description of embodiments thereof, given by way of example only, with reference to the accompanying drawings, in which.

DETAILED DESCRIPTION OF EMBODIMENTS

Figure 1:
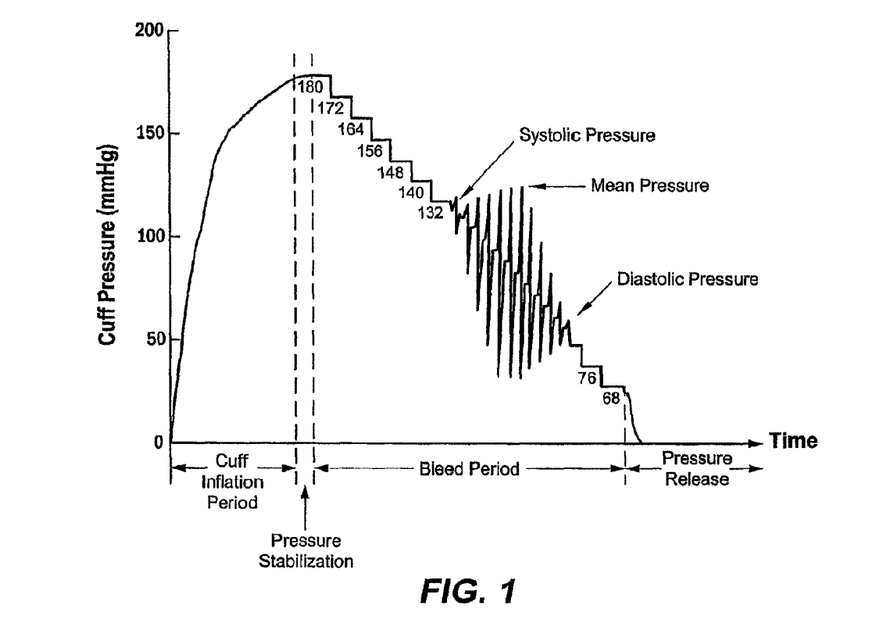
FIG. 1 is a chart showing stages of release of pressure from a blood pressure cuff, illustrating the important blood pressure parameters.

FIG. 1 is a graph which illustrates how systemic arterial blood pressure measurements are made using a conventional blood pressure cuff. The readings may be taken by an automated system or manually, as known.

The cuff is inflated until blood flow in the target vessel (artery in arm, for example) is occluded. Pressure is then released in a controlled fashion, as illustrated by curve 1 in FIG. 1. Note that pressure may be released in a stepwise fashion (each step forming a "bleed point") or in a continuous fashion. The less the number of bleed points available, or the shorter the continuous release curve over the operating pressure range (60 mm Hg to 180 mm Hg for a human), the less scope is allowed for error and the more likely significant error will occur in the blood pressure reading.

As the pressure is released, onset of oscillations is identified and a reading of systolic arterial pressure taken. Mean and diastolic pressures are also determined (diastolic pressure when the oscillations cease and full blood flow is occurring).

This conventional approach is subject to error, and the errors become particularly significant where there are large variations between limb/extremity size relative to the size and therefore volume of the cuff. This is particularly the case for small human patients, particularly infants, and small animals.

Figure 2:
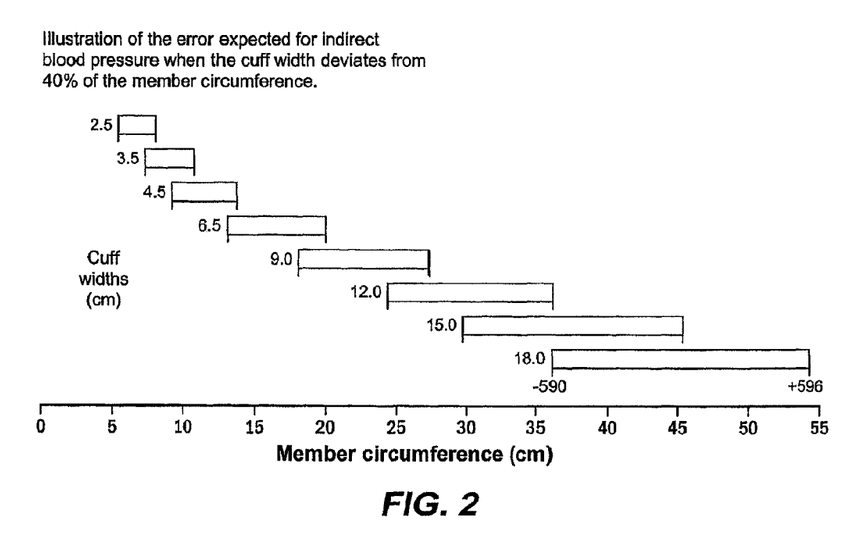
FIG. 2 is a graph showing the ranges of errors that may occur in blood pressure readings for various sizes of cuff and patient limb.

FIG. 2 illustrates the range of errors that may occur with the conventional approach. It can be seen that the errors may be very significant. In the worst cases, the blood pressure measurement cannot be relied upon.

The errors occur for two major reasons. Firstly, because of large variations in limb size relative to cuff width and volume for smaller cuffs and smaller patients. Secondly, the possibility of error is inherently increased by the use of a small volume cuff, (such as a paediatric or neonatal cuff for example, which may have a volume of typically between 30 to 50 mls). As a result of their smaller volume, such cuffs experience a far more rapid drop in pressure once the bleed valve is opened, in comparison to larger volume adult duffs. A rapid or steep drop in pressure makes it difficult to obtain an accurate reading of the exact point for systole and diastole readings and therefore makes repeatability unreliable. This also means that there will be less bleed points available to the operator (again resulting in a steeper curve which may fail to intersect the systolic (peak of blood pressure waveform) and diastolic (trough) points).

Figure 4:
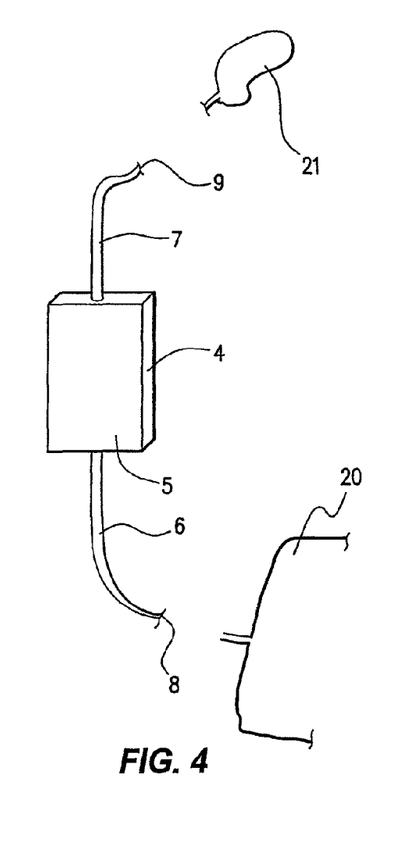
FIG. 4 is a diagram of an apparatus in accordance with an embodiment of the present invention.

An apparatus in accordance with an embodiment of the present invention is illustrated in FIG. 4. The apparatus includes a fluid reservoir 4, in the example being in the form of a plastics container 4, having flexible walls 5. In this embodiment, the plastics container 4 is made of silicone and is rectilinear in shape. However, it is noted that the container 4 is not limited to this shape and could be any convenient shape.

The apparatus in this embodiment includes one or more tubes 6, 7 (in this case there are two tubes 6 and 7) which define passageways 8, 9, in fluid communication with the fluid in the container 4 (note that the fluid in this embodiment is air, but it could be any suitable fluid). The tubes 6, 7 enable the container 4 to be connected in a line to a blood pressure cuff, illustrated schematically in FIG. 4 and designated by reference numeral 20.

In use, the container 4 is connected to a blood pressure cuff 20 which is then inflated (via an inflater 21). The pressure is then released in a controlled manner, as is conventional, in order to obtain blood pressure readings. The fluid reservoir 4 provides an additional fluid volume to the fluid volume of the cuff 20. Further the container 4 has compliance (the walls are expandable and the fluid reservoir may expand to a certain extent). The compliance is arranged so that oscillations in pressure from the blood pressure cuff which occur during a blood pressure reading are not significantly damped in any way and can still be detected so that accurate blood pressure measurements may be made.

In this embodiment, the compliance of the fluid container 4 is such that pressure during the blood pressure measurement does not exceed the critical opening pressure of the container.

The fluid container 4 must provide a compliance to allow some change in volume which can facilitate the change in volume of the cuff 20. It should not, however, inject or add any pressure (or any significant pressure) to the blood pressure measurement system. In other words, the compliance provides a change in volume without a (significant) change in pressure. This results in an effective additional volume being provided to the volume of the blood pressure cuff which effectively makes the bleed period (FIG. 1) shallower, as compared with utilising the cuff volume on its own. That is, it will provide more "steps" for determining the intersection point on the blood pressure curve for the systole (peak) and diastole (trough) blood pressure reading.

Figure 5:
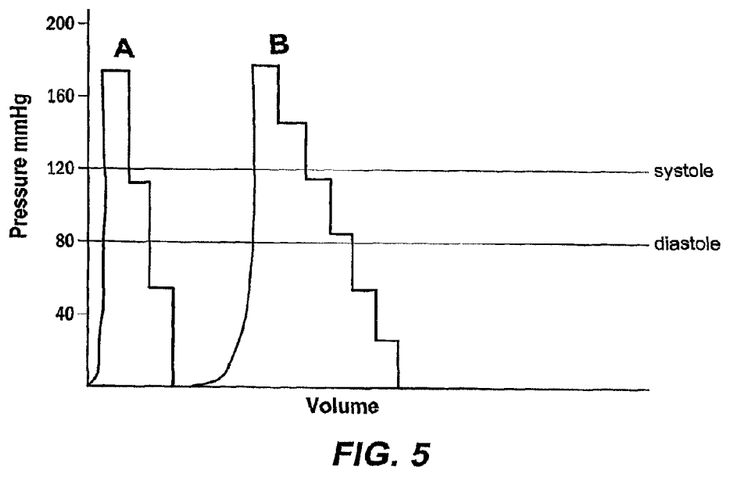
FIG. 5 is a graph illustrating an effect of providing an additional fluid volume for blood pressure measurement, in accordance with an embodiment of the present invention.

FIG. 5 illustrates the effect of adding in the fluid reservoir. Curve A shows the pressure release curve for a low volume cuff. It can be seen that the pressure release curve is steep, leading to potential inaccuracies.

Curve B illustrates the same pressure release curve but with an additional (compliant) volume added into the blood pressure measurement system. In this case, the volume is doubled. It can be seen that the B pressure release curve is shallower than A and therefore there is more scope for obtaining an accurate blood pressure reading. For a neonatal pneumatic cuff, with a working volume of 12 mls to 20 mls, this effect can be achieved by the addition of a low compliance reservoir with a working volume (in the 60 mm Hg to 140 mm Hg pressure range) of 25 mls to 40 mls.

Figure 6:
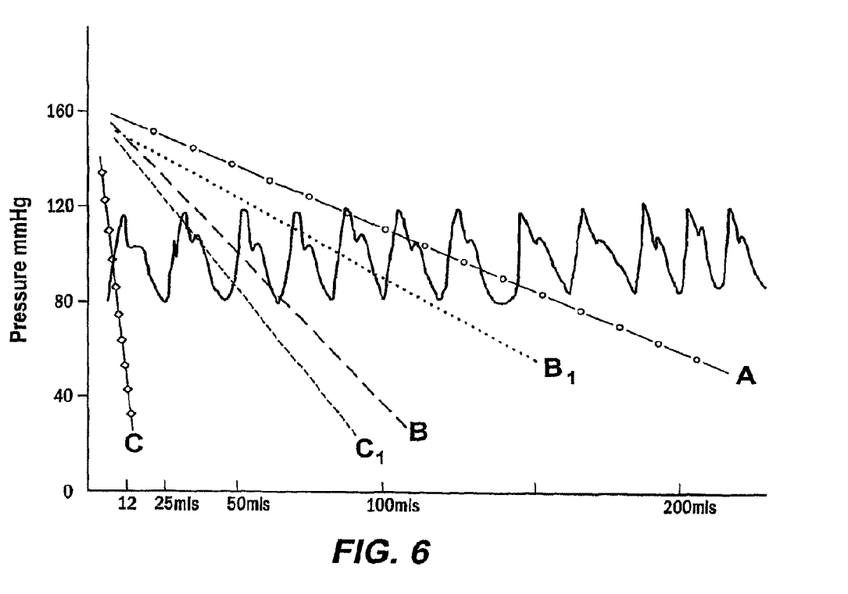
FIG. 6 is a graph illustrating the effect on accuracy of pressure determination by providing the additional volume.

FIG. 6 shows the effect of pneumatic cuff volume on accuracy of pressure determination from the blood pressure wave form for a fixed rate of deflation from 160 mm Hg of the pneumatic cuff, for a number of different situations.

A is the curve for an adult pneumatic cuff, with a working volume of 200 mls.

is for a child's pneumatic cuff, with a working volume of 75 mls to 100 mls (accuracy is lower).

$B_1$ shows a child's cuff with the addition of a low compliance reservoir (in accordance with an embodiment of the present invention) of 25 mls to 30 mls working volume, giving a total volume of 100 mls to 130 mls. It can be seen that accuracy is slightly increased.

C shows an infant pneumatic cuff with a working volume of 15 mls $C_1$ shows an infant cuff plus a low compliance reservoir giving a total volume of 40 mls to 45 mls (and giving an increase in accuracy). In this case the volume of the neo-natal cuff is 15 ml, so the additional volume (25 mm-40 mm) will result in a curve slope more than two times less steep.

This embodiment of the present invention operates, together with a blood pressure cuff, to reduce errors in blood pressure readings due to the extra volume provided by the fluid reservoir. It is particularly useful for situations where errors with conventional blood pressure measurement are likely to be large, such as with small humans and animals. It is not limited to these situations, however, and the fluid reservoir may still be of use with adult humans and large animals.

Figure 3:
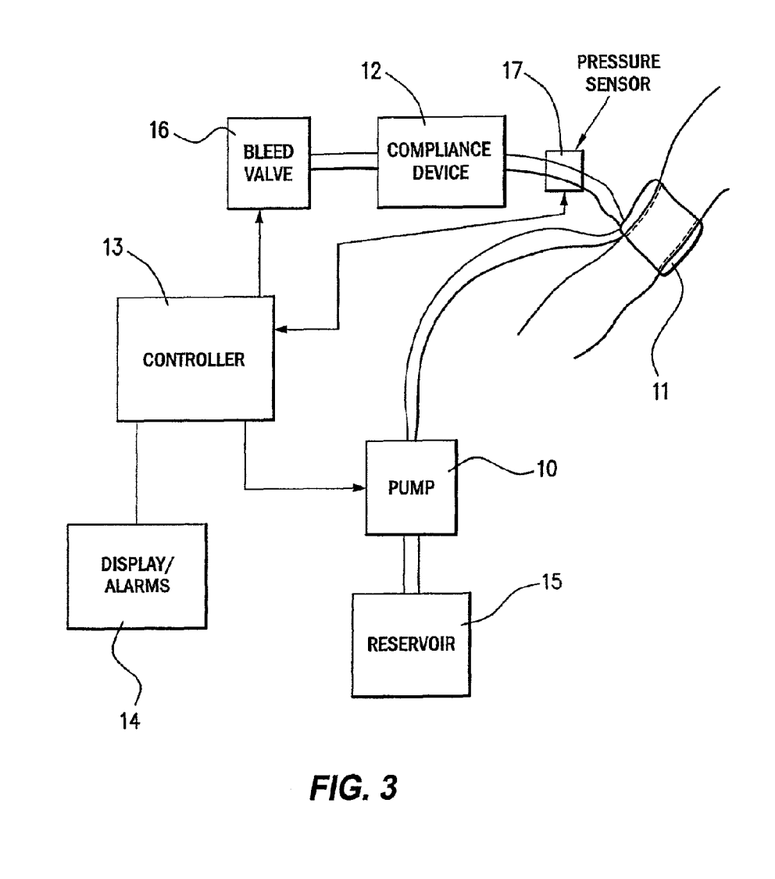
FIG. 3 is a block diagram of an automated system in accordance with an embodiment of the present invention.

FIG. 3 illustrates an automated system for measuring blood pressure. The system includes a pump 10 for providing fluid (air) under pressure to a cuff 11. A fluid reservoir 12 (termed a "compliance device" in this embodiment) having compliance is also connected in the system. A controller 13 controls the measurement of blood pressure. A display 14 provides readings. In operation, the controller 13 controls the pump 10 to pump air from a reservoir 15 into the pressure cuff 11. Controller 13 subsequently controls a bleed valve 16 to apply a controlled release from the cuff 11. A pressure sensor 17 detects pressure oscillations within the cuff, whereby the controller can make blood pressure measurements.

In this embodiment, the compliance device 12 is in the pressure line and provides an additional compliant volume which improves the accuracy of the blood pressure measurement.

Figure 7:
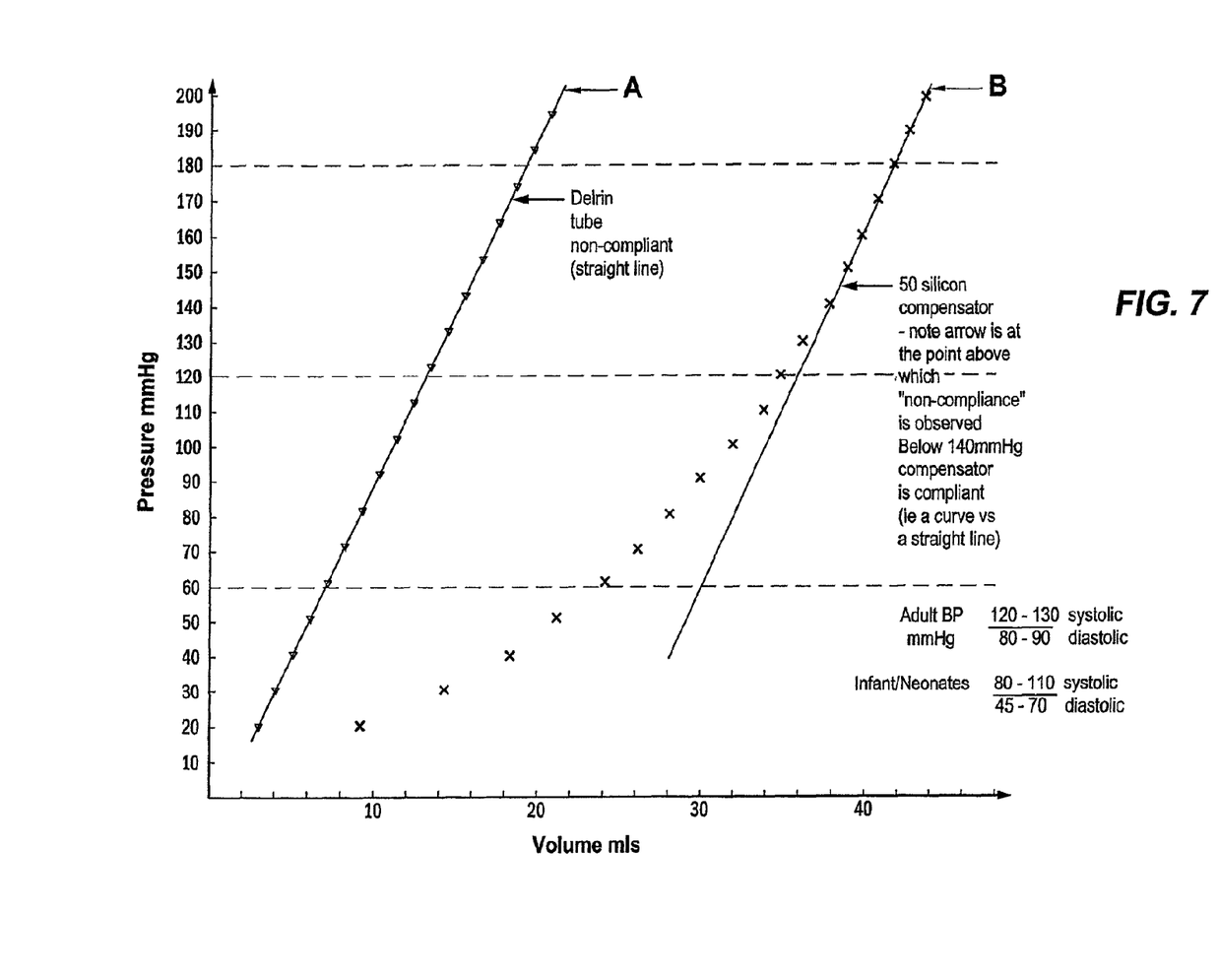
FIG. 7 is a "compliance curve" illustrating properties of compliance of a fluid reservoir in accordance with an embodiment of the present invention.

FIG. 7 is a graph which illustrates the compliance curve for a fluid reservoir in accordance with an embodiment of the present invention.

Curve A illustrates pressure against volume for a non-compliant Delrin tube (the Delrin cylinder is 85 mm tall and 23 mm in diameter in this example). It can be seen that Delrin tube is non compliant. The Delrin tube has a similar total volume to the compliant container. If it were used in the present invention it would not provide an appropriate additional volume for increasing the accuracy of blood pressure measurement.

On the other hand, curve B shows a curve for a 45 mm by 10 mm by 100 mm long with 2 mm wall thickness fluid reservoir (made from silicone) in accordance with an embodiment of the present invention. Arrow 50 shows a point above which non-compliance is observed. Below 134 mm Hg, the fluid reservoir compensator is compliant (i.e. a curve as opposed to a straight line). This means that the compliant wall of the compensator has not been "stretched", therefore it will not exert elastic energy and therefore positive pressure on the pneumatic cuff. Additionally, the slope of the straight line portion of this curve (above 100 to 140 mm Hg) is not a vertical line, indicating that the critical opening pressure of the device has not been reached.

Figure 8:
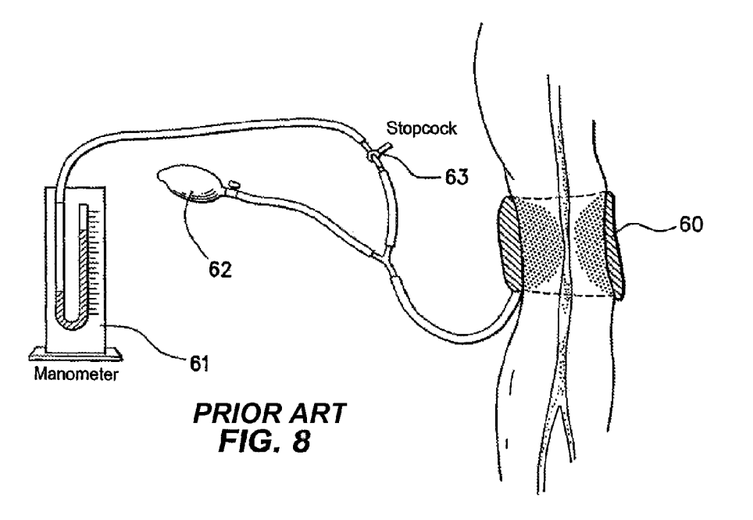
FIG. 8 is a diagram illustrating a conventional measurement system for measuring blood pressure.

FIG. 8 illustrates a typical current blood pressure measurement system (manual system) using a pneumatic cuff 60 on the forearm and a pressure manometer 61 to measure pressure. The return of pulsation is detected either by a pressure change on the manometer (oscillations) or by ausculting the artery with a stethoscope. A bulb 62 enables manual pumping to increase pressure in the cuff 60. Stop cock 63 enables the controller to release the pressure.

Figure 9:
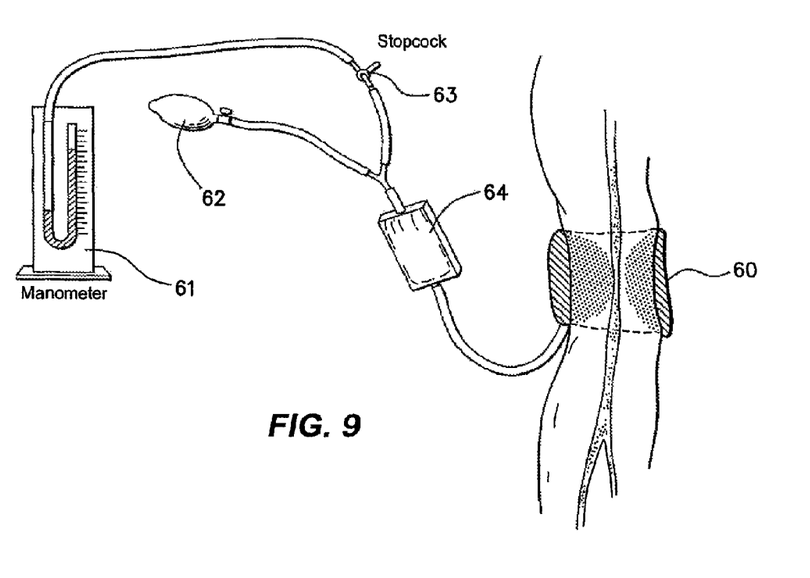
FIG. 9 is a diagram illustrating manual measurement of blood pressure using an apparatus in accordance with an embodiment of the present invention.

FIG. 9 illustrates a manual blood pressure measurement system incorporating a compliant fluid reservoir 64 in accordance with an embodiment of the present invention, in the pressure line. The fluid reservoir 64 expands as the cuff is inflated to increase the potential volume by 25 mls to 40 mls (over an operating range of 60 mm Hg to 180 mm Hg).

Figure 10:
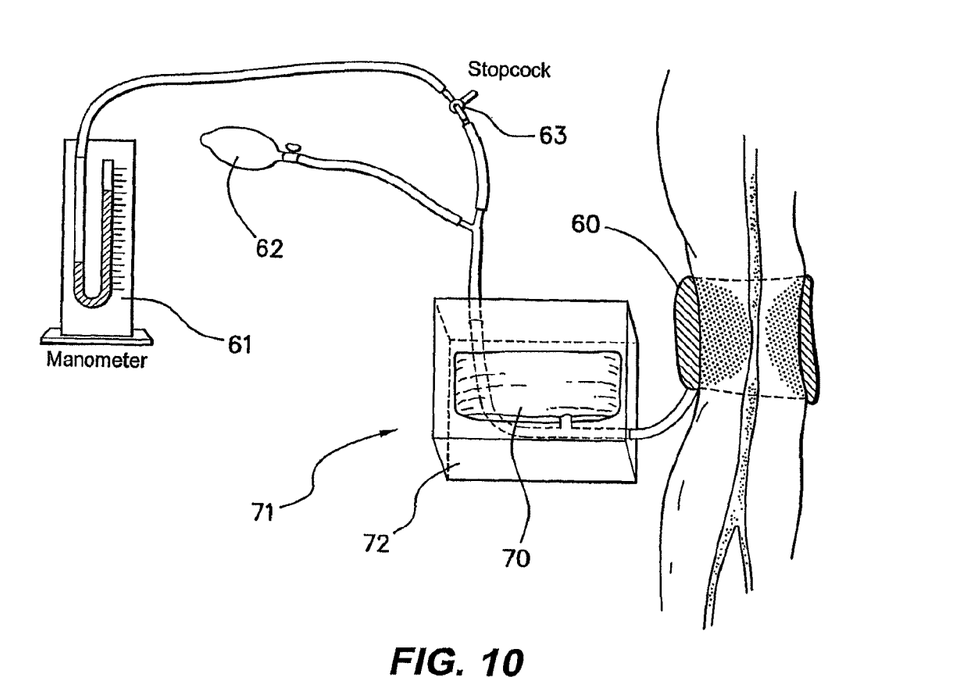
FIG. 10 is a diagram illustrating manual measurement of blood pressure using an apparatus in accordance with a further embodiment of the present invention.

FIG. 10 illustrates a manual blood pressure measurement system incorporating a compliant fluid reservoir 70 in accordance with a further embodiment of the present invention. Other components of the measurement system are as in FIG. 8 and FIG. 9, and the same reference numerals have been used.

In this embodiment, the fluid reservoir forms part of an arrangement generally designated by reference numeral 71, which includes the fluid reservoir 70 and a rigidly walled container 72. The fluid reservoir 70 may be a further blood pressure cuff, or may be of similar material. Expansion of the fluid reservoir 70 past its critical opening pressure is prevented, or limited by the walls of the rigid container 72 to prevent the arrangement from going over a certain volume.

The above described embodiment of the present invention is applied in measurement of systemic arterial blood pressure. The present invention is not limited to measurement of blood pressure. It can be used to measure any pressures, for example in the human or animal body. It is particularly useful to increase the relative volume of a pressure measurement system, particularly where the system demonstrates small pressure changes in small volume situations.

For example, embodiments of the present invention may be used in the following applications:

1. Measuring the profile of pressure in the bladder.
2. Uretheral pressure profilometry.
3. To measure the pressure in a patient's airways e.g. in treatment of asthma.
4. Measurement of oesophagal pressure.
5. Measurement of pressure in cerebral spinal fluid.

It is also envisaged that the present invention could equally be used for pressure measurement in non-biological systems where pressure is being detected as volume changes. For example, it could be useful in testing changes in pressure or volume in a small volume system, such as a component of an anaesthetic machine. Adding the compliant volume results in making the pressure/volume curve less steep so that the tester is more likely to find a correct end point. Small pipes or reservoirs holding fluids such as water may also be tested using this invention, and other non-biological systems.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:

1. An apparatus for facilitating blood pressure measurement, including a fluid reservoir arranged to be connected in fluid communication with a blood pressure arm cuff, the fluid reservoir providing an additional fluid volume to the fluid volume of the cuff during measurement of blood pressure of a patient, and wherein the fluid reservoir has a compliance such that the fluid reservoir is arranged to change volume when a change of pressure is applied, adding little or no pressure back into the system comprising the fluid reservoir and the blood pressure cuff, when the fluid reservoir changes volume, and the fluid reservoir being operable during deflation of the blood pressure cuff to slow the rate of change in pressure, and wherein the compliance is arranged such that oscillations of pressure from the blood pressure cuff are not damped by the fluid reservoir, wherein the fluid reservoir is arranged to expand as the blood pressure cuff is inflated to increase the potential volume by 25 mls to 40 mls over an operating range of 60 mm Hg to 180 mm Hg, and the apparatus further including a controller that controls measurement of blood pressure in a deflation mode.

2. The apparatus in accordance with claim 1, wherein the compliance is arranged such that the pressure on the fluid reservoir during any blood pressure measurement does not exceed the fluid reservoir's Critical Opening Pressure.

3. The apparatus in accordance with claim 1, wherein the fluid reservoir includes a fluid container having at least one expandable wall providing compliance.

4. The apparatus in accordance with claim 3, wherein the fluid container is of flexible plastic material.

5. A system for measuring blood pressure, including an apparatus in accordance with claim 1 and a blood pressure cuff, the fluid reservoir being arranged to be connected in fluid communication with the blood pressure cuff.

6. An automated system for measuring blood pressure, including a controller for controlling the provision of fluid under pressure to a blood pressure cuff, a display for providing a reading of blood pressure value, and an apparatus in accordance with claim 1, the fluid reservoir being connected in fluid communication with the blood pressure cuff.

7. A method of measuring blood pressure using a blood pressure arm cuff, including the step of providing an additional fluid volume in fluid connection with the blood pressure cuff, the additional fluid volume having a compliance such that the additional fluid volume is arranged to change volume when a change of pressure is applied, adding little or no pressure back into the system comprising the fluid volume and the blood pressure cuff when the fluid volume changes volume, the additional fluid volume being operable during deflation of the blood pressure cuff to slow the rate of change in pressure, and wherein the additional volume is formed by a fluid reservoir, wherein the compliance is arranged such that oscillations of pressure from the blood pressure cuff are not damped by the fluid reservoir, wherein the fluid reservoir is arranged to expand as the blood pressure cuff is inflated to increase the potential volume by 25 mls to 40 mls over an operating range of 60 mm Hg to 180 mm Hg, and the method further including controlling measurement of blood pressure in a deflation mode.

8. The method in accordance with claim 7, wherein the additional fluid volume is arranged to change the effective volume of the blood pressure cuff when a change of pressure is applied.

9. The method in accordance with claim 7, wherein the compliance is sufficient such that oscillations of pressure from the blood pressure cuff are not significantly damped.

10. The method in accordance with claim 7, wherein the additional volume is formed by a fluid reservoir and the compliance is such that the pressure on the fluid reservoir during any blood pressure measurement will not exceed the fluid reservoir's Critical Opening Pressure.

11. An apparatus for facilitating blood pressure measurement, including a fluid reservoir arranged to be connected in fluid communication with a blood pressure arm cuff, the fluid reservoir providing an additional fluid volume to the fluid volume of the cuff during measurement of blood pressure of a patient, and wherein the fluid reservoir has a pressure dependent compliance such that the fluid reservoir changes volume when a change of pressure is applied to slow the change in pressure that occurs as gas is released from the blood pressure cuff during a gas bleed off portion of a blood pressure measurement, and wherein the compliance is arranged such that oscillations of pressure from the blood pressure cuff are not damped by the fluid reservoir, wherein the fluid reservoir is arranged to expand as the blood pressure cuff is inflated to increase the potential volume by 25 mls to 40 mls over an operating range of 60 mm Hg to 180 mm Hg, and the apparatus further including a controller that controls measurement of blood pressure in a deflation mode.

12. A method of making a blood pressure measurement on a subject comprising:

simultaneously placing gas in a first gas reservoir of a blood pressure arm cuff and a second compliant gas reservoir coupled to the first gas reservoir in the blood pressure cuff until the pressure in the reservoirs is above the systolic pressure of the subject; and opening a valve to simultaneously release gas from the first gas reservoir of the blood pressure arm cuff and the second compliant gas reservoir such that the pressure drops in a continuous or stepwise manner through the systolic and diastolic pressures of the subject, wherein the compliant gas reservoir changes volume as the pressure drops to reduce the rate of the pressure drop through the systolic and diastolic pressures, and wherein the compliance of the reservoirs are arranged such that oscillations of pressure from the blood pressure cuff are not damped by the reservoirs, wherein the reservoirs are arranged to expand as the blood pressure cuff is inflated to increase the potential volume by 25 mls to 40 mls over an operating range of 60 mm Hg to 180 mm Hg, and the method further including controlling measurement of blood pressure in a deflation mode.

13. The apparatus in accordance with claim 1, wherein the blood pressure arm cuff is configured to be placed around a limb of a human or animal patient.

* * * * *